(12) United States Patent
Kobayashi

(10) Patent No.: US 6,342,295 B1
(45) Date of Patent: Jan. 29, 2002

(54) MOISTURE SENSOR

(75) Inventor: Nobuo Kobayashi, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 09/468,913

(22) Filed: Dec. 22, 1999

(30) Foreign Application Priority Data

Dec. 28, 1998 (JP) ............................................ 10-377081
Dec. 28, 1998 (JP) ............................................ 10-377082

(51) Int. Cl.$^7$ ................................................. B32B 5/16
(52) U.S. Cl. .................... 428/323; 428/425.9; 428/913; 73/29.01; 73/335.02; 73/335.05; 338/35
(58) Field of Search .................... 338/34, 35; 428/323, 428/328, 423.1, 425.9, 479.4, 480, 913; 73/29.01, 335.02, 335.03, 335.04, 335.05

(56) References Cited

U.S. PATENT DOCUMENTS

| 3,983,527 A | 10/1976 | Ohsato et al. ................. 338/36 |
| 5,050,434 A | 9/1991 | Demisch ................... 73/335.04 |
| 5,122,237 A | 6/1992 | Kim et al. ................... 205/107 |

FOREIGN PATENT DOCUMENTS

| DE | 39 19 864 | 12/1990 |
| DE | 41 24 149 | 2/1992 |
| DE | 40 35 371 | 5/1992 |
| DE | 44 03 409 | 8/1995 |
| JP | 61-33374 | 8/1986 |
| JP | 62-53064 | 11/1987 |
| JP | 9-5274 | 1/1997 |

OTHER PUBLICATIONS

U.S. application Ser. No. 08/982,890, filed Dec. 2, 1997.

*Primary Examiner*—Blaine Copenheaver
*Assistant Examiner*—Christopher Paulraj
(74) *Attorney, Agent, or Firm*—Oblon, Spivak, McClelland, Maier & Neustadt, P.C.

(57) ABSTRACT

A moisture sensor includes a moisture-sensitive film between a pair of electrodes having conductive particles dispersed in a hygroscopic polymer. The hygroscopic polymer is a polymer comprising a polyether amine, an epoxy compound, and optionally a water-soluble nylon. Alternatively, the hygroscopic polymer is a polyether ester amide and optionally a water-soluble nylon. The sensor enables DC measurement, can detect a humidity in the range of RH 60% to 100%, and ensures high performance stability against repetitive operations.

20 Claims, 12 Drawing Sheets

FIG. 7
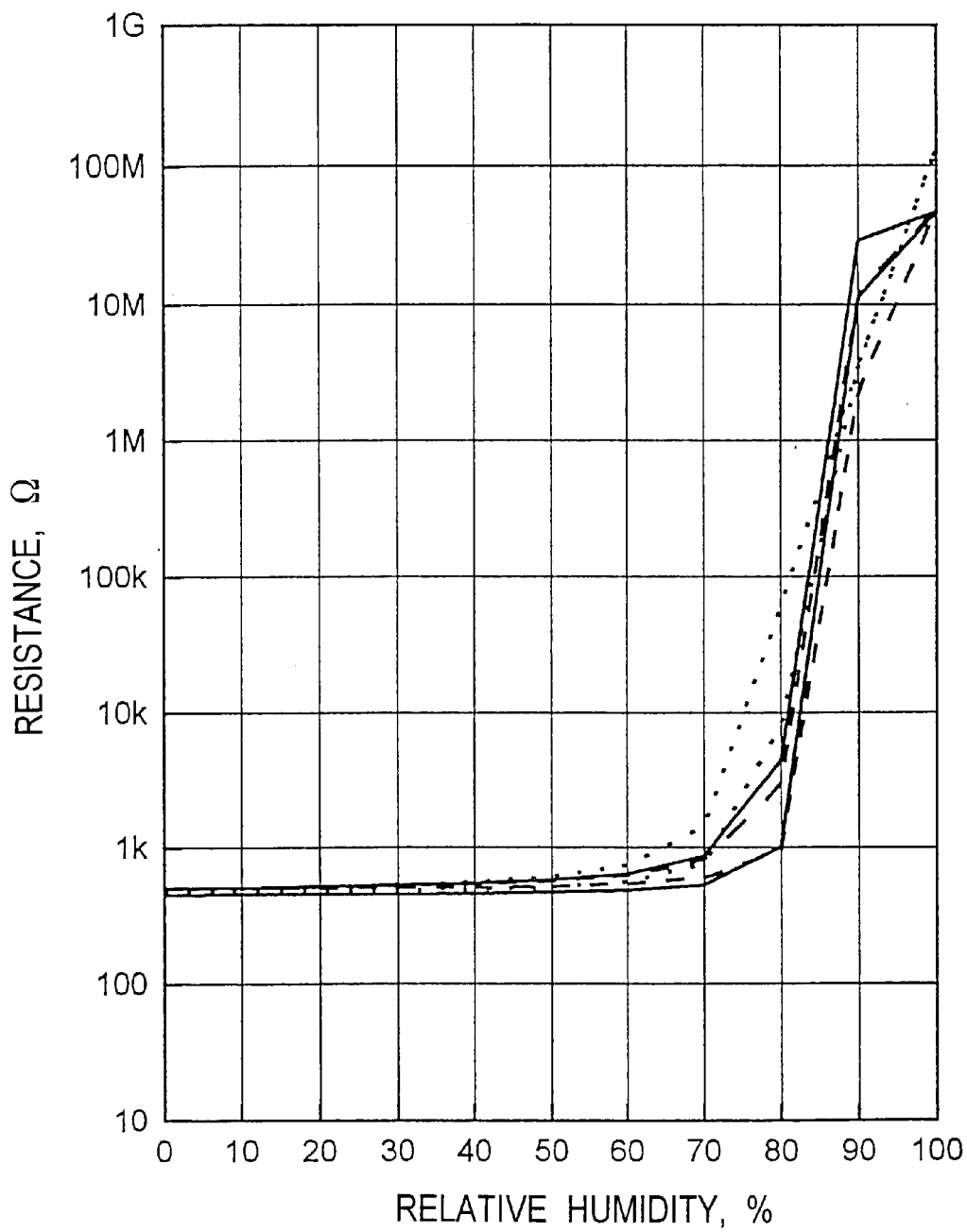
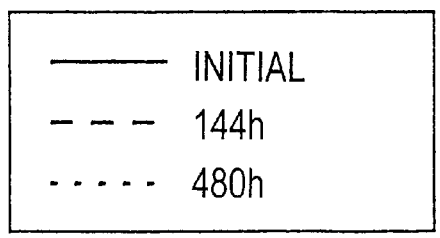

EXAMPLE 10

| | |
|---|---|
| —— | INITIAL |
| - - - | 144h |
| ⋯⋯ | 480h |

FIG. 9
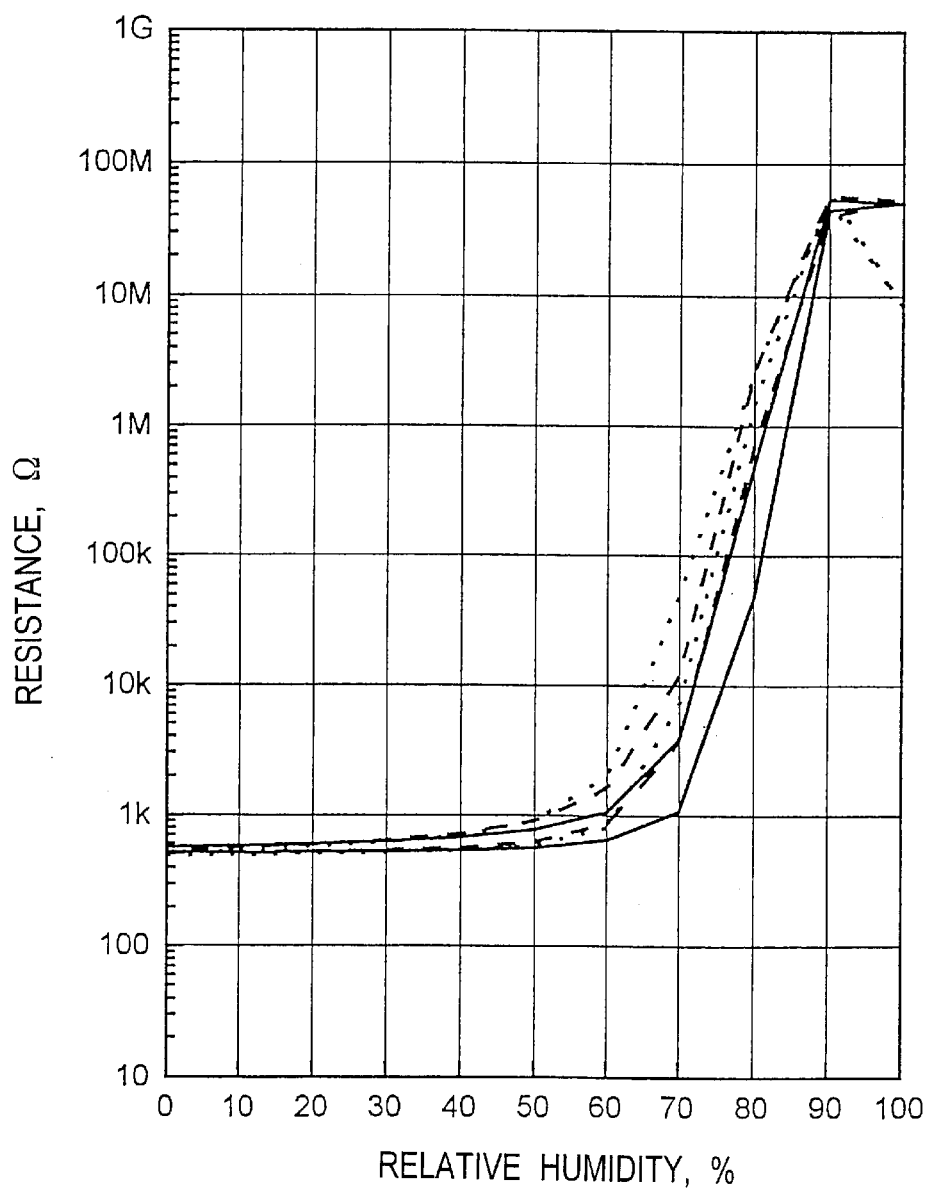
EXAMPLE 11
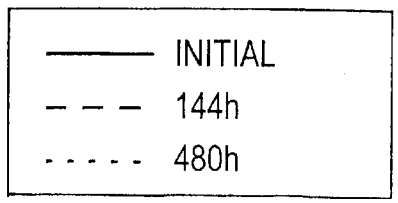

FIG. 10
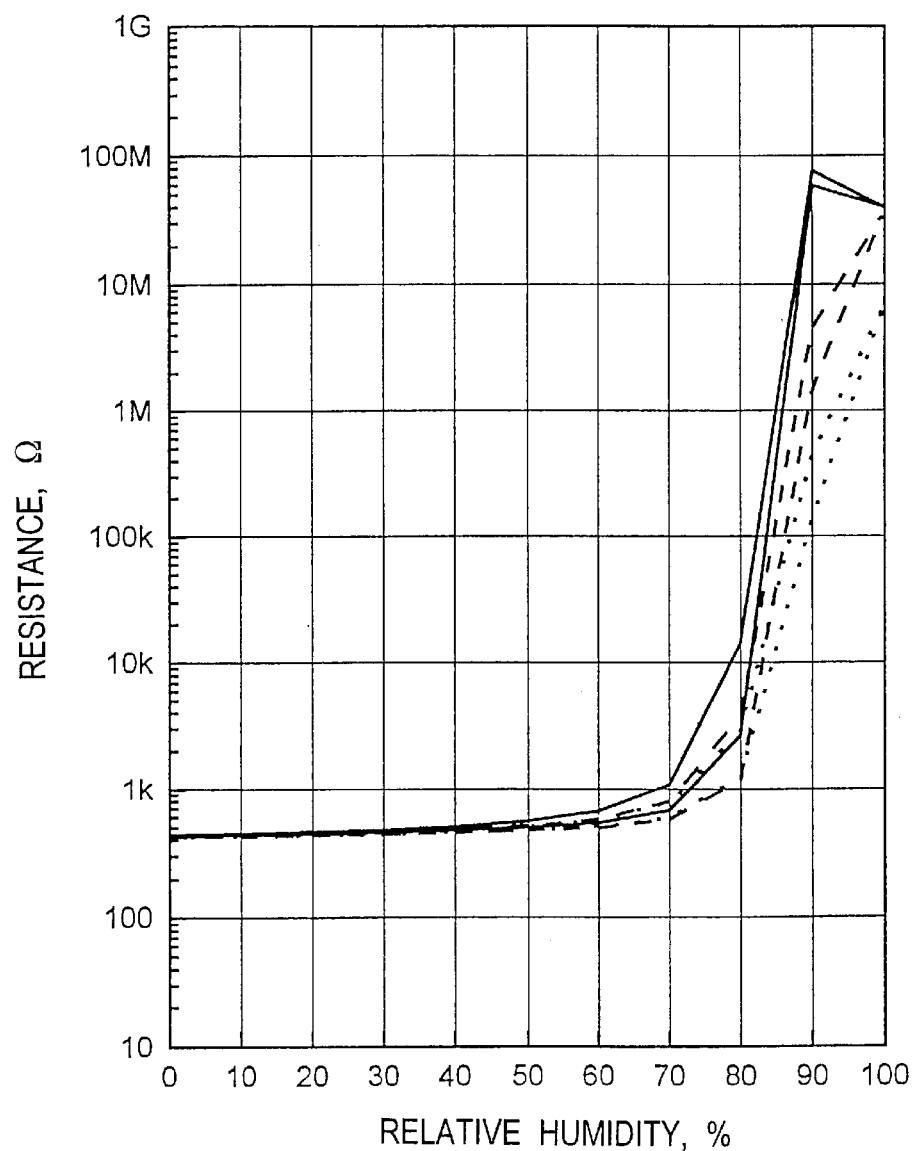
EXAMPLE 12
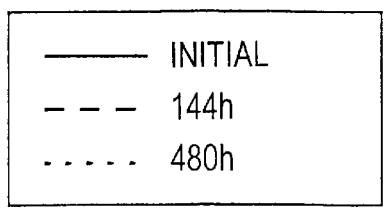

FIG. 11
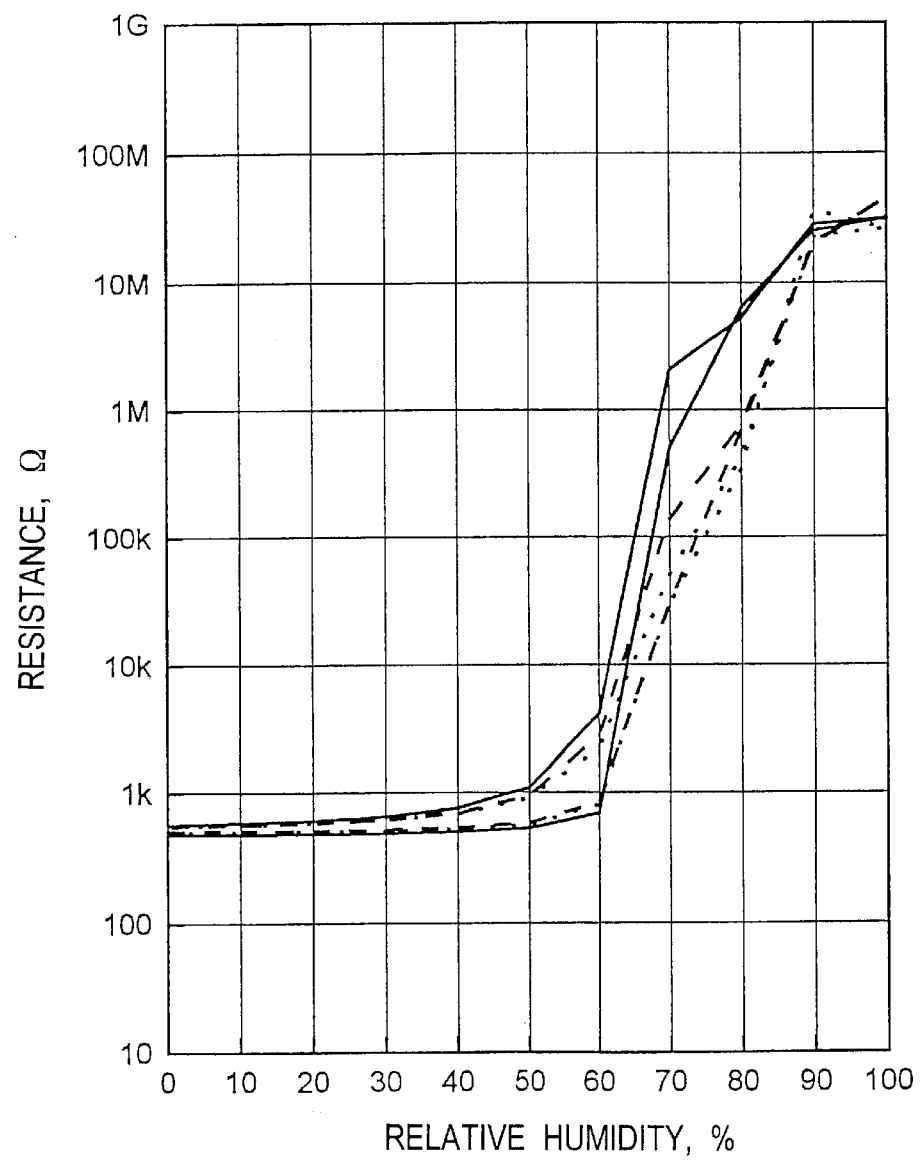
EXAMPLE 13
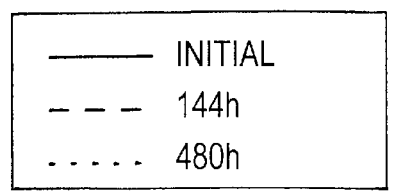

FIG. 12
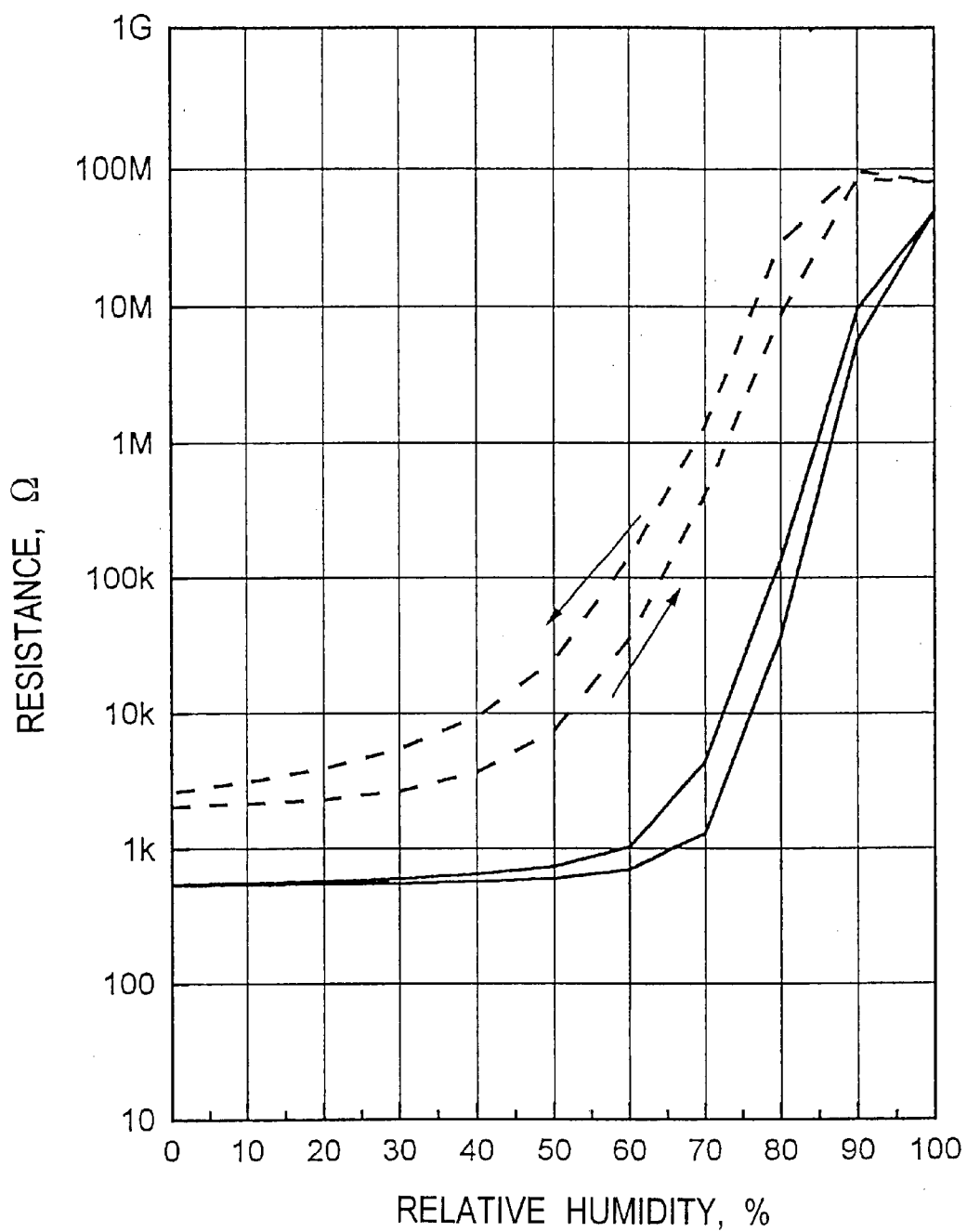
EXAMPLE 2
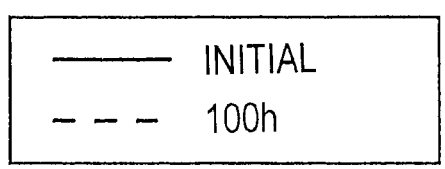

MOISTURE SENSOR

This invention relates to a moisture sensor comprising a moisture-sensitive film having conductive particles dispersed in a hygroscopic polymer.

BACKGROUND OF THE INVENTION

Among known moisture sensors for detecting humidity and moisture condensation, those comprising a moisture-sensitive film having conductive particles dispersed in a hygroscopic polymer are disclosed in JP-A 58-99740, 59-170755, 60-250241, 62-21052 and 6-249813. These moisture sensors are designed such that at a low humidity, conductive particles are in contact with each other to form conductive paths, providing a low resistance, but at a high humidity, the hygroscopic polymer absorbs moisture and swells thereby to interrupt conductive paths, changing to a high resistance state.

Another example of the moisture sensors using hygroscopic polymers is a moisture sensor comprising a polymer electrolyte having quaternary ammonium base whereby a change of its ionic conductivity is utilized (see JP-A 7-318526). This moisture sensor detects a humidity in an environment under observation by utilizing the phenomenon that the degree of dissociation of counter ions to the quaternary ammonium base varies with the level of moisture in the environment to change the ionic current flow upon application of voltage. However, the moisture sensor utilizing the change of ionic conductivity requires AC for measurement and thus needs a complex circuit. Additionally, the sensor performance is unstable in that at a high humidity above relative humidity (RH) 90%, especially under a moisture condensing atmosphere, the sensor is less resistant to water because the polymer electrolyte can be partially dissolved out. Another problem causing unstable performance is the hysteresis phenomenon that the sensor produces different output values at the same humidity depending on whether the humidity is increasing or decreasing.

By contrast, the aforementioned moisture sensors having conductive particles dispersed in a hygroscopic polymer have the advantage that the measurement circuit is simplified because of possible DC measurement. The sensors of this type, however, can detect only a range from RH 90% to moisture condensation, the detectable range being limited to a high humidity region. The hygroscopic polymers used in the prior art are hydroxymethacrylate and polyvinyl alcohol, which abruptly increase their water pickup when the surrounding humidity is beyond RH 90%. The sensor fails to produce a sufficient resistance value at a humidity below RH 90% and is thus low sensitive in the low humidity region.

JP-B 61-33374 discloses a moisture-sensitive resistor having conductive particles dispersed in an alcohol-soluble copolymerized polyamide resin. This resistor starts to increase its resistance at about RH 60%. Once exposed to a high humidity atmosphere, the resistor cannot resume the original resistance change and shows a resistance about twice the initial resistance value. The polyamide resin starts moisture absorption at a relatively low humidity, but the moisture pickup itself is small. In order to increase the change of resistance of the moisture sensor relative to a humidity change, the loading of conductive particles must be reduced. This leads to the drawback that the sensor shows high and unstable resistance values under dry conditions. The sensor of JP-B 61-33374 showed a resistance of about 5 kΩ and a resistance change of about 3.5 places under dry conditions, which are still insufficient.

None of the moisture sensors comprising a moisture-sensitive film having conductive particles dispersed in a hygroscopic polymer are successful in achieving stable detection of a humidity below RH 90%. In the application where moisture sensors are incorporated in air conditioners and humidifiers, needed are moisture sensors which can detect a humidity not only in the high humidity region above RH 90%, but also in a low humidity region, especially in the humidity region of RH 60% to 90%.

SUMMARY OF THE INVENTION

Therefore, an object of the invention is to provide a moisture sensor which allows for DC-measurement, can detect a humidity in a region below RH 90%, especially in the humidity region of RH 60% to 100%, and ensures high performance stability against repetitive operations. Another object of the invention is to provide a moisture sensor which experiences little deterioration of performance even when kept in a high temperature, high humidity atmosphere.

The invention is directed to a moisture sensor comprising a pair of electrodes and a moisture-sensitive film disposed therebetween having conductive particles dispersed in a hygroscopic polymer.

In a first embodiment, the hygroscopic polymer is a polymer comprising a polyether amine having at least two amino groups and an epoxy compound having at least two epoxy groups and an ether bond. Preferably, the polyether amine has a polyether skeleton consisting of propylene oxide, ethylene oxide or a mixture thereof; the polyether amine is terminated with two or three primary amino groups; the polyether amine has a molecular weight of 100 to 5,000. Also preferably, the epoxy compound is of the following formula (1):

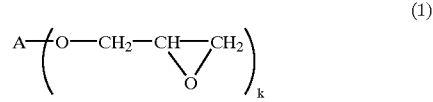

(1)

wherein A is a di- to tetra-valent aliphatic saturated hydrocarbon group, aliphatic ether group or heterocyclic group, and k is an integer of 2 to 4. Further preferably the hygroscopic polymer has an amine equivalent and an epoxy equivalent which are in a ratio of from 1:1 to 1:4.

In one preferred embodiment, the hygroscopic polymer is a polymer comprising the polyether amine, the epoxy compound, and a water-soluble nylon, or a mixture of the polymer between the polyether amine and the epoxy compound and a water-soluble nylon. The preferred water-soluble nylon has an ether structure. The water-soluble nylon is preferably comprised of units of the following formula (7) or units of the following formula (8) or both:

(7)

(8)

wherein $R_1$ is an alkyl group of 2 to 4 carbon atoms. An appropriate content of the water-soluble nylon is 0.1 to 50% by weight based on the weight of the polyether amine and the epoxy compound combined.

In a second embodiment, the hygroscopic polymer comprises a polyether ester amide. The polyether ester amide is preferably of the following formula (2):

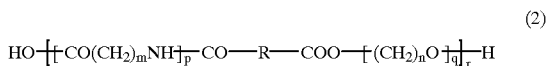

(2)

wherein R is an alkyl group of 2 to 12 carbon atoms, m is an integer of 6 to 12, n is an integer of 1 to 4, p is an integer of 1 to 70, q is an integer of 5 to 200, and r is an integer of at least 3, and especially m is equal to 11 and n is equal to 2.

In one preferred embodiment, the hygroscopic polymer is a polymer comprising the polyether ester amide, a water-soluble nylon, and an epoxy compound having at least two epoxy groups, or a mixture of the polyether ester amide and a water-soluble nylon. The preferred features of the water-soluble nylon are as described above. An appropriate content of the water-soluble nylon is 0.1 to 50% by weight based on the weight of the polyether ester amide.

Typically, the conductive particles are carbon black particles having a specific surface area of 30 to 300 $m^2/g$.

The moisture sensor can detect a humidity in the range of RH 60% to RH 100%.

BRIEF DESCRIPTION OF THE DRAWINGS

FIGS. 6 to 11 are graphs showing the humidity-resistance response of moisture sensors of Examples 8 to 13 at the initial and after aging in a 60° C./RH 95% atmosphere, respectively.

FIG. 12 is a graph showing the humidity-resistance response of the moisture sensor of Example 2 at the initial and after aging in a 60° C./RH 95% atmosphere.

DESCRIPTION OF THE PREFERRED EMBODIMENTS

Figure 1:
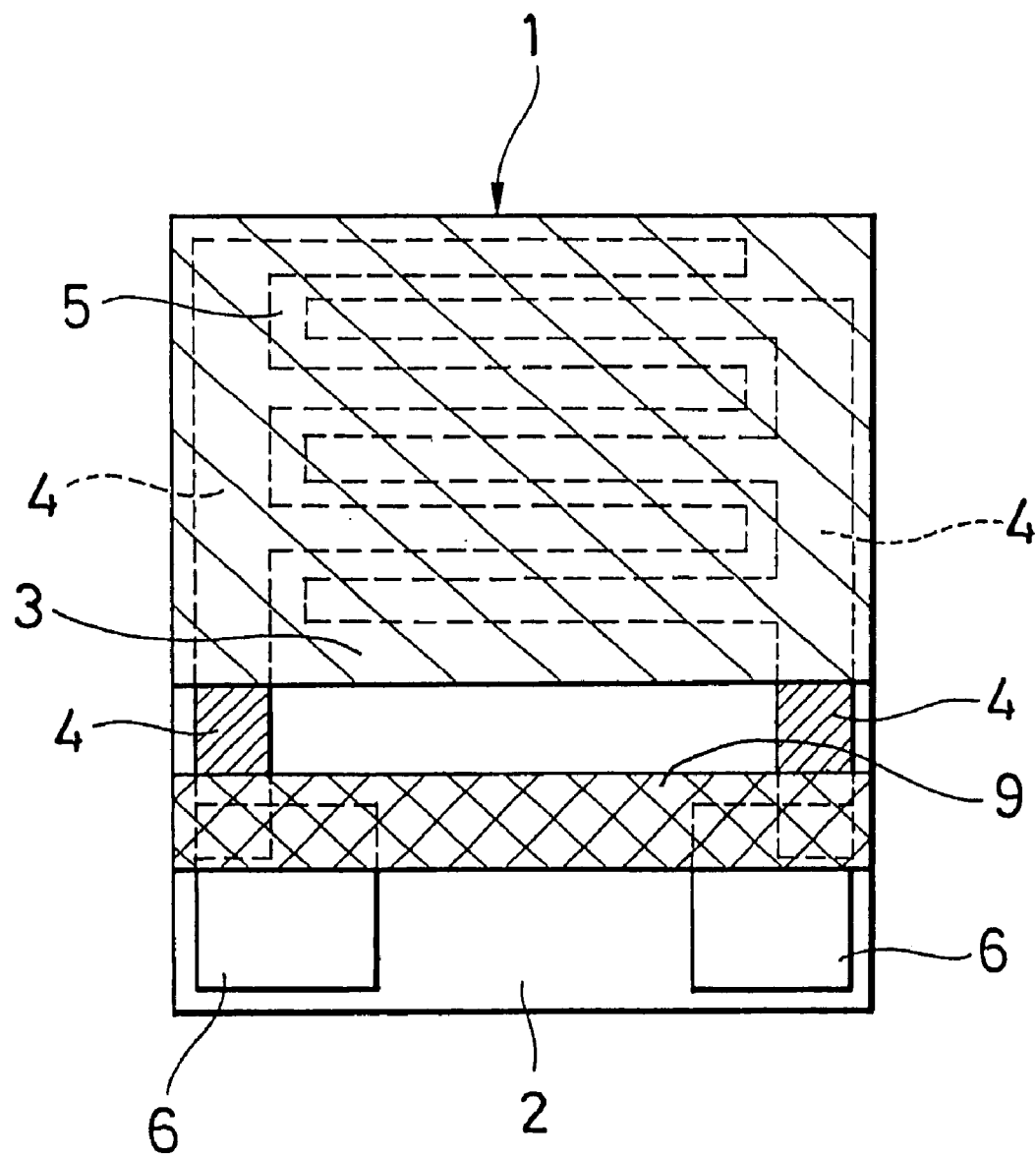
FIG. 1 is a plan view showing one exemplary construction of the moisture sensor of the invention.

The moisture sensor of the invention has a moisture-sensitive film between a pair of electrodes. The moisture-sensitive film has conductive particles dispersed in a hygroscopic polymer.

First Embodiment

In the first embodiment, the hygroscopic polymer is obtained by polymerizing a polyether amine having at least two amino groups with an epoxy compound having at least two epoxy groups and an ether bond.

The polymer between a polyether amine having at least two amino groups with an epoxy compound having at least two epoxy groups and an ether bond starts to absorb moisture in a humidity region below relative humidity (RH) 90%, especially in a humidity region of from RH 60% to less than RH 90%. This enables detection of a humidity not only in the high humidity region above RH 90%, but also in a low humidity region below RH 90%. The moisture sensor of the invention is especially effective in detecting a humidity in the humidity region of RH 60% to 90%.

In one preferred embodiment, the hygroscopic polymer is a polymer comprising a polyether amine having at least two amino groups, an epoxy compound having at least two epoxy groups and an ether bond, and a water-soluble nylon. In another preferred embodiment, the hygroscopic polymer is a mixture of a water-soluble nylon and a polymer comprising a polyether amine having at least two amino groups and an epoxy compound having at least two epoxy groups and an ether bond. Also acceptable are combinations of these embodiments, that is, combinations of a polyether amine/epoxy compound/nylon polymer with a mixture of a polyether amine/epoxy compound polymer and a nylon. Preferably, the water-soluble nylon has an ether bond so that the nylon is more hydrophilic. It is generally believed that in the polyether amine/epoxy compound/nylon polymer, the polyether amine and the epoxy compound are graft polymerized to the water-soluble nylon.

Since the polymer has a moisture pickup as high as 10 to 20% by weight, the polymer allows a larger amount of conductive particles to be loaded, leading to stable humidity-resistance characteristics. The hygroscopic polymer used herein exerts hygroscopicity primarily at the ether bond (—O—) while amino and hydroxyl groups provide some contribution thereto. Under dry conditions, the moisture sensor of the invention shows sufficient and stable characteristics as demonstrated by a resistance of about 400Ω to about 2 kΩ and a resistance change of about 4 to 6 places (i.e., $10^4$ to $10^6$). If the water-soluble nylon has an ether bond, the polymer has a correspondingly increased moisture pickup.

Additionally, the moisture sensor of the invention maintains its humidity-resistance characteristics quite stable even when exposed to and cycled between a dry atmosphere and a highly humid atmosphere, showing a very little change of performance even after 400 cycles.

In the preferred embodiment wherein the nylon is polymerized or admixed with the polyether amine/epoxy compound polymer, the moisture sensor experiences only a very little change of its humidity-resistance response even when exposed to a high temperature, high humidity atmosphere for a long period of time. Using as the hygroscopic polymer a polymer between a polyether amine having at least two amino groups and an epoxy compound having at least two epoxy groups and an ether bond (being free of a water-soluble nylon) or a water-soluble nylon provides a moisture sensor which can detect a humidity below RH 90% and whose performance is stable against cycling between a dry atmosphere and a highly humid atmosphere. However, exposure to a high temperature, high humidity atmosphere for a long period of time can cause the moisture sensor using a polyether amine/epoxy compound polymer as the hygroscopic polymer to undergo a gradual increase of resistance. Exposure to a high temperature, high humidity atmosphere for a long period of time can cause a moisture sensor using a water-soluble nylon as the hygroscopic polymer to undergo a gradual decline of resistance. The moisture sensor can be made more resistant to long-term exposure to a high temperature, high humidity atmosphere by using as the hygroscopic polymer a polyether amine/epoxy compound/water-soluble nylon polymer or a mixture of a polyether amine/epoxy compound polymer and a water-soluble nylon.

The use of a moisture-sensitive film having conductive particles dispersed in a hygroscopic polymer enables DC measurement, with the advantages of a simple measurement circuit and a low cost.

Polyether Amine

First described is the polyether amine used in the hygroscopic polymer. The polyether amine, also designated polyoxyalkylene amine, is a compound of polyether skeleton terminated with primary amino groups.

The polyether skeleton is any of alkylene oxides, preferably propylene oxide (PO) or ethylene oxide (EO) or a mixture (EO/PO) of ethylene oxide and propylene oxide. In the EO/PO mixture, the ratio of EO/PO is not critical although a higher EO/PO ratio is effective for detecting a lower humidity. Polymers having EO skeletons are fully soluble in water, and polymers consisting of EO skeletons are significantly more reactive than the other polymers. When polymers having EO skeletons are used, an increase of resistance starts from a lower humidity, but there is a tendency that the stability against repetitive operation lowers.

The polyether amine should have at least two terminal amino groups, and preferably two or three amino groups. Namely, diamines and triamines are preferable.

Preferably the polyether amine has a molecular weight of 100 to 5,000, and especially 100 to 2,000. With too high a molecular weight, there is a tendency that the resistance starts to increase at a higher humidity. A mixture of polyether amines, when used, preferably has a number average molecular weight (Mn) within the above range.

The polyether amine in diamine form is synthesized by reacting a dihydric alcohol with an alkylene oxide, preferably propylene oxide and/or ethylene oxide and converting terminal hydroxy groups into amino groups. The diols used herein include ethylene glycol and propylene glycol.

The polyether amine in triamine form is synthesized by reacting a triol initiator with an alkylene oxide, preferably propylene oxide and converting terminal hydroxyl groups into amino groups. Exemplary triol initiators are trimethylol propane and glycerol.

Preferably the polyether amine used herein has an overall amine equivalent of 0.3 to 15 meq/g, and especially 2 to 10 meq/g. It is also preferred that at least 95% of the polyether amine used is primary amine. With a higher amine equivalent beyond the range, the resulting polymer may have an excessively high crosslink density, which tends to reduce the moisture pickup and hence, sensitivity. With a lower amine equivalent below the range, the resulting polymer tends to have a lower crosslink density and lower water resistance.

Further preferably the polyether amine used herein has a flash point of at least 100° C., especially 120 to 300° C. Polyether amines with a lower flash point may be less safe.

The polyether amine may contain up to 0.5%, preferably up to 0.25% by weight of water.

Examples of the polyether amine include polyoxymethylene amine, polyoxyethylene amine of the following formula (3), polyoxypropylene amines of the following formulae (4) and (5), and polyoxyethylene propylene amine of the following formula (6). Their derivatives are also useful. The polyether amines may be used alone or in admixture of two or more. When a mixture of two or more polyether amines is used, their mixing ratio is arbitrary.

(3)

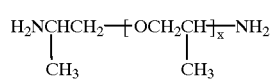

(4)

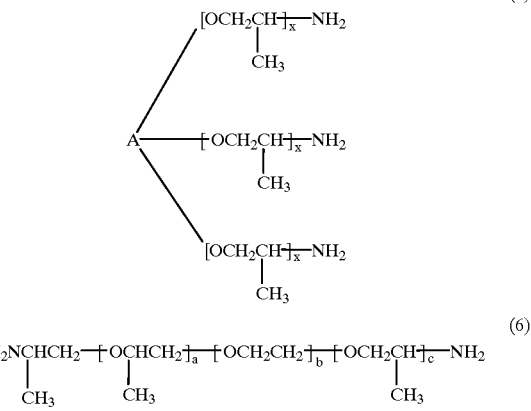

Note that x, a, b and c are arbitrary integers.

The polyether amines used herein are commercially available. For example, polyoxypropylene diamine is available under the trade name of Jeffamine D-230, 400, 200 and 4000, polyoxyethylene diamine is available under the trade name of Jeffamine EDR-148, polyoxyethylene propylene diamine is available under the trade name of Jeffamine ED-600, 900, and 2003, and polyoxypropylene triamine is available under the trade name of Jeffamine T-403, 3000 and 5000, all from Texaco Chemical Inc.

Epoxy Compound

Also used in the hygroscopic polymer is an epoxy compound. The epoxy compound used herein has at least two epoxy groups, preferably two to four epoxy groups, and an ether bond. The inclusion of an ether bond enhances hydrophilic property.

Preferred epoxy groups are 1,2-epoxide although 1,3-epoxide, 1,4-epoxide, and 1,5-epoxide are also acceptable. Epoxy compounds having two to four glycidyl groups are preferable, with epoxy compounds of the following formula (1) being especially preferable.

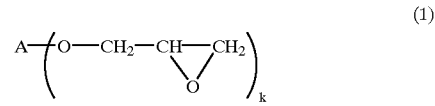

(1)

In formula (1), A is a di- to tetra-valent aliphatic saturated hydrocarbon group, aliphatic ether group or heterocyclic group, and k is an integer of 2 to 4. The carbon chain represented by A may be branched or substituted with hydroxyl or other groups. Exemplary groups are given below.

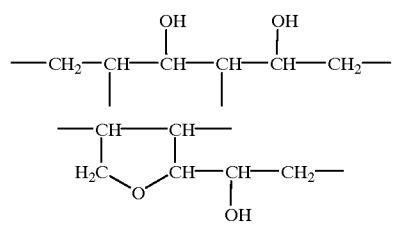

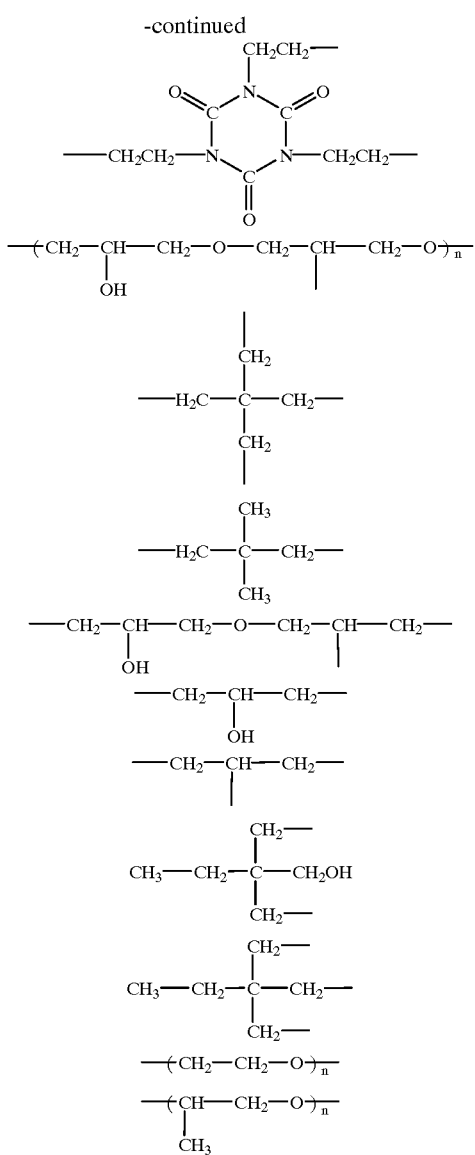

Examples of the epoxy compound having such an ether structure include sorbitol polyglycidyl ether, sorbitan polyglycidyl ether, polyglycerol polyglycidyl ether, pentaerythritol polyglycidyl ether, diglycerol polyglycidyl ether, triglycidyl tris(2-hydroxyethyl)isocyanurate, glycerol polyglycidyl ether, trimethylol propane polyglycidyl ether, neopentyl glycol diglycidyl ether, ethylene glycol diglycidyl ether, polyethylene glycol diglycidyl ether, propylene glycol diglycidyl ether, and polypropylene glycol diglycidyl ether. Derivatives of these compounds are also useful. The epoxy compounds may be used alone or in admixture of two or more. When a mixture of two or more epoxy compounds is used, their mixing ratio is arbitrary.

The epoxy compounds used herein are commercially available. For example, sorbitol polyglycidyl ether is commercially available under the trade name of Denacol EX-611, 612, 614 and 614B, sorbitan polyglysidyl ether is commercially available under the trade name of Denacol EX-651 and 651A, polyglycerol polyglycidyl ether is commercially available under the trade name of Denacol EX-512 and 521, pentaerythritol polyglycidyl ether is commercially available under the trade name of Denacol EX-411, diglycerol polyglycidyl ether is commercially available under the trade name of Denacol EX-421, triglycidyl tris(2-hydroxyethyl)isocyanurate is commercially available under the trade name of Denacol EX-301, glycerol polyglycidyl ether is commercially available under the trade name of Denacol EX-313 and 314, trimethylol propane polyglycidyl ether is commercially available under the trade name of Denacol EX-321, neopentyl glycol diglycidyl ether is commercially available under the trade name of Denacol EX-211, ethylene glycol diglycidyl ether is commercially available under the trade name of Denacol EX-810 and 811, polyethylene glycol diglycidyl ether is commercially available under the trade name of Denacol EX-850, 851, 821, 830, 832, 841 and 861, propylene glycol diglycidyl ether is commercially available under the trade name of Denacol EX-911, and polypropylene glycol diglycidyl ether is commercially available under the trade name of Denacol EX-941, 920, 921 and 931, all from Nagase Chemicals K.K.

Preferably the epoxy compound used herein has an epoxy equivalent of 50 to 700 WPE, and especially 100 to 250 WPE. With a higher epoxy equivalent beyond the range, the resulting polymer may have an excessively high crosslink density, which tends to reduce the moisture pickup and hence, sensitivity. With a lower epoxy equivalent below the range, the resulting polymer tends to have a lower crosslink density and lower water resistance.

The epoxy compound used herein preferably has a water dissolution of 15 to 100%, especially 20 to 100%. With a lower water dissolution below the range, the detectable humidity level may become higher and sometimes exceed RH 90%. The term "water dissolution" is a percent of a resin fraction dissolved when 10 parts by weight of a resin is added to 90 parts by weight of water at 25° C.

Further preferably the epoxy compound used herein has a flash point of at least 90° C., especially 120 to 300° C. Epoxy compounds with a lower flash point may be less safe.

The epoxy compound may contain up to 25%, preferably up to 15% by weight of chlorine etc.

In the invention, the polymerized product of the above-mentioned polyether amine and epoxy compound is used as the hygroscopic polymer. Polymerization is effected according to the following scheme using an alcohol or water as the catalyst.

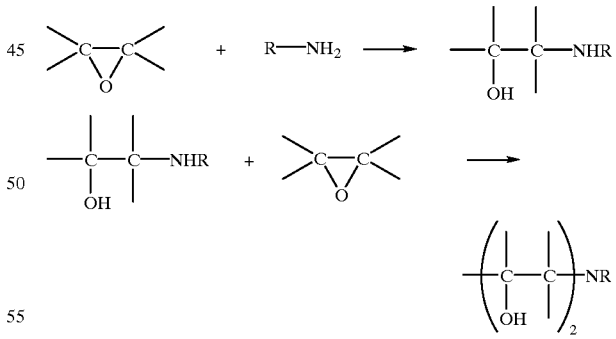

More particularly, polymerization is effected by adding a polyether amine and an epoxy compound to alcohol or water in such amounts that the concentration of the compounds combined may be 10 to 80% by weight, preferably 30 to 60% by weight, dispersing the compounds in a dispersing medium, and heating the dispersion at a temperature of about 80 to 180° C., especially about 120 to 160° C. for a time of about ½ to 3 hours, especially about 1 to 2 hours. The dispersing medium may be ethyl cellosolve or ethylene glycol. Polymerization conditions may be selected as appropriate depending on the particular type of polyether amine and epoxy compound used and are not limited to the above range. As will be described later, one typical procedure involves adding conductive particles to the dispersing medium along with the polyether amine and epoxy compound, coating the dispersion, and heating the coating to cause polymerization.

With respect to the composition of the polyether amine and the epoxy compound having an ether structure, it is preferred from the standpoint of performance stability that these compounds are mixed such that the amine equivalent and the epoxy equivalent may be in a ratio of 1:1 to 1:4, especially equal. The humidity-resistance response may be controlled by shifting the composition from the equivalent ratio of 1:1. A composition containing an excess of the amine has a tendency that the resistance increases at a lower humidity, but the performance stability declines.

The polymer of polyether amine and epoxy compound should preferably have a water absorption of 4 to 20%, especially 6 to 15% at 25° C. and RH 80%. A polymer having a higher percent water absorption beyond the range experiences a greater change of resistance, but has a possibility that after it is exposed to the high humidity region, the resistance is kept increased and prevented from resuming the original value. A polymer having a lower percent water absorption below the range may not fully swell upon moisture absorption, leading to a lower sensitivity.

Nylon

Optionally, a water-soluble nylon is used in the hygroscopic polymer. The water-soluble nylon used herein preferably has an ether bond, and is more preferably comprised of units of the following formula (7) or units of the following formula (8) or both.

(7)

(8)

In formula (7), $R_1$ is an alkyl group of 2 to 4 carbon atoms, preferably an ethylene group having 2 carbon atoms.

The water-soluble nylon preferably has a degree of polymerization of 5 to 100, especially 10 to 50.

The proportion of units of formula (7) to units of formula (8) is such that there is present up to 50 parts, especially up to 10 parts by weight of units of formula (8) per 100 parts by weight of units of formula (7). A homopolymer consisting of units of formula (7) may be used herein.

The water-soluble nylon has such a water solubility that at least 1 part, especially at least 10 parts by weight of the nylon is dissolved in 100 parts by weight of water. With a lower solubility below the limit, a moisture-sensitive film tends to be reduced in water pickup and sensitivity.

The water-soluble nylon is prepared by cyano-ethylating a polyalkylene glycol, hydrogenating the glycol to form a diamine, forming a salt (known as nylon salt) of the diamine with adipic acid, and reacting the nylon salt with caprolactam. Illustratively, synthesis can be made in accordance with JP-A 60-247440.

The water-soluble nylon comprising units of the formula (7) and/or (8) is commercially available under the trade name of P-70 and A-90 from Toray K.K.

One typical process for polymerizing a polyether amine, an epoxy compound and a water-soluble nylon involves dissolving the nylon in alcohol or water in a concentration of 0.1 to 60% by weight, especially 0.5 to 30% by weight, adding the polyether amine and the epoxy compound thereto in a total concentration of 10 to 80% by weight, especially 30 to 60% by weight, dispersing the components in a dispersing medium, and heating the dispersion at about 80 to 180° C., especially about 120 to 160° C., for about ½ to 3 hours, especially about 1 to 2 hours. The dispersing medium may be ethyl cellosolve or ethylene glycol. Polymerization conditions may be selected as appropriate depending on the particular type of polyether amine, epoxy compound and nylon used and are not limited to the above range. As will be described later, in one preferred practice, conductive particles are also added to the dispersing medium along with the polyether amine, epoxy compound and nylon, followed by coating the dispersion, and heating the coating to cause polymerization.

It is generally believed that in the resulting polymer, the polyether amine and epoxy compound are graft polymerized to the water-soluble nylon. It is acceptable that the nylon is not polymerized during the process and the nylon is left in admixture with a polymer of the polyether amine and the epoxy compound.

Preferably the water-soluble nylon is used in an amount of 0.1 to 50%, especially 1 to 10% by weight based on the weight of the polyether amine and the epoxy compound combined. If the content of nylon exceeds the range, the resulting film tends to experience a gradual lowering of resistance when exposed to a high temperature, high humidity atmosphere for a long period of time. If the content of nylon is below the range, the resulting film tends to experience a gradual increase of resistance when exposed to a high temperature, high humidity atmosphere for a long period of time.

The polymer of a polyether amine, an epoxy compound and a water-soluble nylon or the mixture of a polyether amine/epoxy compound polymer and a water-soluble nylon should preferably have a water absorption of 4 to 20%, especially 6 to 15% at 25° C. and RH 80%. A higher percent water absorption beyond the range results in a greater change of resistance, but has a possibility that after the film is exposed to the high humidity region, the resistance is kept increased and prevented from resuming the original value. A polymer or mixture having a lower percent water absorption below the range may not fully swell upon moisture absorption, leading to a lower sensitivity.

In order to enhance the effectiveness of the polyether amine/epoxy compound polymer, a hydrophobic or water-repellent substance may be added. Exemplary additives are silicone fluids, especially silicone fluids modified with functional groups such as amino and epoxy groups, and long-chain alkyls having functional groups. Although a polyether amine/epoxy compound polymer having a higher percent water absorption has a possibility that once it is exposed to the high humidity region, the resistance is kept increased and prevented from resuming the original value as mentioned above, the addition of a hydrophobic or water-repellent substance restrains such possibility. An appropriate amount of the hydrophobic or water-repellent substance added is up to about 30% by weight, especially about 3 to 20% by weight based on the polymer. With a more amount of the hydrophobic or water-repellent substance, the moisture-sensitive film may be reduced in water absorption and hence, sensitivity. The silicone fluid used herein preferably has a functional group equivalent of 100 to 2,000 g/mol, especially 200 to 1,000 g/mol. The same applies to the polyether amine/epoxy compound/nylon polymer or the mixture of a polyether amine/epoxy compound polymer and a nylon in the preferred embodiment.

Second Embodiment

In the second embodiment of the invention, a polyether ester amide is used as the hygroscopic polymer. The polyether ester amide is preferably of the formula (2) shown below. The use of polyether ester amide gives the same results as in the first embodiment (using a polymer between a polyether amine having at least two amino groups and an epoxy compound having at least two epoxy groups and an ether bond). The polyether ester amide enables detection of a humidity not only in the high humidity region of RH 90% or above, but also in a low humidity region below RH 90%. The moisture sensor using the same is especially effective in detecting a humidity in the humidity region of RH 60% to 100%. Since the polyether ester amide has a moisture pickup as high as 10 to 20% by weight, it allows a larger amount of conductive particles to be loaded, leading to a stable humidity-resistance response. The humidity-resistance response is very stable even when the sensor is exposed to and cycled between a dry atmosphere and a highly humid atmosphere.

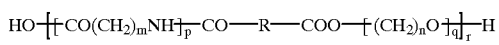

The polyether ester amide has a linear, ordered chain-like structure consisting of hard polyamide segments and soft polyether segments. Owing to the two different segments included, it possesses excellent mechanical and physical properties. The polyether ester amide is obtained by reacting a polyamide diacid oligomer with a polyether diol oligomer.

Useful examples of the polyether ester amide used herein are described in French Patent Nos. 2,273,021, 2,401,947 and 2,384,810, Japanese Patent Publication No. 45(1970)-7559, U.S. Pat. Nos. 4,345,064, 4,349,661, 4,345,052, French Patent Application No. 91 03175, and JP-A 7-102062. Also useful are those compounds described in EP 0,378,015 and 0,476,963 and JP-A 10-158509.

Preferably the polyether ester amides used herein are those of the above formula (2). In formula (2), R is an alkylene group of 2 to 12 carbon atoms, preferably 6 to 12 carbon atoms. The alkylene group represented by R may be straight or branched. The alkylene group may further have a substituent(s) although unsubstituted alkylene is preferred. Exemplary are methyl, ethyl, n-propyl, isopropyl, n-butyl, isobutyl, sec-butyl and tert-butyl. The letter m is an integer of 6 to 12, preferably 6 to 11, n is an integer of 1 to 4, preferably 2 or 3, p is an integer of 1 to 70, preferably 5 to 30, q is an integer of 5 to 200, preferably 10 to 100, and r is an integer of at least 3, preferably 3 to 1,000. It is especially preferred that in formula (2), m be equal to 11 and n be equal to 2.

With respect to the degree of polymerization (p) of polyamide segments and the degree of polymerization (q) of polyether segments, it is preferred that q be greater than or equal to p. If the polyamide segments are longer than the polyether segments, a reduction of water pickup and hence, sensitivity is likely to occur.

The polyether ester amide should preferably have a water absorption of 0.3 to 10%, especially 3 to 8% at 20° C. and RH 65%. A polymer having a higher percent water absorption beyond the range experiences a greater change of resistance, but has a possibility that after it is exposed to the high humidity region, the resistance is kept increased and prevented from resuming the original value. A polymer having a lower percent water absorption below the range may not fully swell upon moisture absorption, leading to a lower sensitivity.

The polyether ester amides of formula (2) have a melting point of about 120 to 210° C., preferably about 160 to 210° C. All the polyether ester amides have a glass transition temperature (Tg) of about −60° C. It is noted that the melting point is attributable to the polyamide phase and the Tg is attributable to the polyether phase.

Such polyether ester amides are commercially available under the trade name of PEBAX 33 series 12 series, 62 series and 11 series from Atochem.

In one preferred embodiment, a mixture of a polyether ester amide as defined above and a water-soluble nylon is used as the hygroscopic polymer. Alternatively, a polymer comprising a polyether ester amide, a water-soluble nylon and an epoxy compound having at least two epoxy groups is used. It is noted that the epoxy compound is used to enable polymerization between the polyether ester amide and the nylon. The use of the polyether ester amide/nylon polymer or mixture gives the same results as in the first embodiment. The polyether ester amide/nylon polymer or mixture enables detection of a humidity not only in the high humidity region of RH 90% or above, but also in a low humidity region below RH 90%. The moisture sensor using the same is especially effective in detecting a humidity in the humidity region of RH 60% to 100%. Since the polyether ester amide/nylon polymer or mixture has a moisture pickup as high as 10 to 20% by weight, it allows a larger amount of conductive particles to be loaded, leading to a stable humidity-resistance response. The humidity-resistance response is very stable even when the sensor is exposed to and cycled between a dry atmosphere and a highly humid atmosphere and even when the sensor is exposed to a high temperature, high humidity atmosphere.

Preferably the water-soluble nylon is used in an amount of 0.1 to 50%, especially 1 to 20% by weight based on the weight of the polyether ester amide. If the content of nylon exceeds the range, the resulting film tends to experience a gradual lowering of resistance when exposed to a high temperature, high humidity atmosphere for a long period of time. If the content of nylon is below the range, the resulting film tends to experience a gradual increase of resistance when exposed to a high temperature, high humidity atmosphere for a long period of time.

To effect polymerization between the polyether ester amide and the water-soluble nylon, an epoxy compound having at least two epoxy groups is added. This reaction system generally produces a polymer of polyether ester amide, water-soluble nylon, and epoxy compound, but sometimes a mixture in which some components are partially left non-polymerized.

The epoxy compound having at least two epoxy groups is not critical insofar as the polymerization reaction proceeds. Preferred are epoxy compounds having at least two epoxy groups and an ether bond as used in the hygroscopic polymer in the first embodiment.

The epoxy compound having at least two epoxy groups is preferably used in an amount of 1 to 20% by weight based on the water-soluble nylon and the polyether ester amide combined although the amount is not limited thereto.

The polyether ester amide/nylon mixture or polyether ester amide/nylon/epoxy compound polymer should preferably have a water absorption of 4 to 20%, especially 6 to 15% at 25° C. and RH 80%. A mixture or polymer having a higher percent water absorption beyond the range experiences a greater change of resistance, but has a possibility that after it is exposed to the high humidity region, the resistance is kept increased and prevented from resuming the original value. A mixture or polymer having a lower percent water absorption below the range may not fully swell upon moisture absorption, leading to a lower sensitivity.

One typical process for polymerizing a polyether ester amide, a water-soluble nylon, and an epoxy compound having at least two epoxy groups involves dissolving the nylon in alcohol or water in a concentration of 0.1 to 60% by weight, especially 0.5 to 30% by weight, adding the polyether ester amide and the epoxy compound thereto, dispersing the components in a dispersing medium, and heating the dispersion at about 80 to 180° C., especially about 120 to 160° C., for about ½ to 3 hours, especially about 1 to 2 hours. The dispersing medium may be ethyl cellosolve or ethylene glycol. Polymerization conditions may be selected as appropriate depending on the particular type of polyether ester amide, nylon and epoxy compound used and are not limited to the above range. As will be described later, in one preferred practice, conductive particles are also added to the dispersing medium along with the polyether ester amide, nylon and epoxy compound, followed by coating the dispersion, and heating the coating to cause polymerization.

In the second embodiment as well, a hydrophobic or water-repellent substance may be added. Exemplary additives are silicone fluids, especially silicone fluids modified with functional groups such as amine and epoxy groups, and long-chain alkyls having functional groups. Although a polyether ester amide having a higher percent water absorption has a possibility that after it is exposed to the high humidity region, the resistance is kept increased and prevented from resuming the original value as mentioned above, the addition of a hydrophobic or water-repellent substance restrains such possibility. An appropriate amount of the hydrophobic or water-repellent substance added is up to about 30% by weight, especially about 3 to 20% by weight based on the polyether ester amide. With a more amount of the hydrophobic or water-repellent substance, the moisture-sensitive film may be reduced in water absorption and hence, sensitivity. The silicone fluid used herein preferably has a functional group equivalent of 100 to 2,000 g/mol, especially 200 to 1,000 g/mol. The same applies to the mixture of a polyether ester amide and a nylon or the polyether ester amide/nylon/epoxy compound polymer in the preferred embodiment.

Conductive Particles

The electroconductive particles used herein include carbonaceous particles such as carbon black and graphite, and metal powders such as nickel, gold, silver and copper. Of these, carbon black is especially useful. Carbon black preferably has a specific surface area of 30 to 300 m$^2$/g, more preferably 30 to 150 m$^2$/g, most preferably 30 to 75 m$^2$/g as measured by BET. Other preferred features of carbon black include a mean particle size of primary particles of 20 to 50 nm, a well-developed structure, and a DBP oil absorption of at least 100 ml/100 g and typically up to 150 ml/100 g. Further preferably, the conductive particles have a mean particle size of about 20 nm to about 3 μm (as represented, in the case of non-spherical particles, by the diameter of a circle of the projected area).

In the moisture-sensitive film, the conductive particles are loaded in an amount of 5 to 40% by weight, more preferably 10 to 30% by weight, in the case of carbon black. A film with a less loading of conductive particles may have a too high resistance in dry conditions and changes its resistance value when repeatedly exposed to a dry atmosphere and a highly humid atmosphere. A film with an excessive loading of conductive particles may experience a smaller change of resistance relative to a humidity change, resulting in a moisture sensor having a lower sensitivity. The amount of other conductive particles loaded is approximately the same as carbon black.

Any desired method may be used in preparing the moisture-sensitive film. Typically the film is prepared by coating a liquid dispersion containing the necessary and optional components in a dispersing medium. The dispersing medium is preferably selected from water, alcohols, ethers, and ketones, and mixtures thereof. Screen printing is a typical coating technique.

After a coating is formed, it is cured by heating at a temperature of about 80 to 180° C. for about ½ to 3 hours. Appropriate curing conditions may be selected in accordance with the polyether amine and epoxy compound or the polyether ester amide (and optional nylon) and are not limited to the above set. Under the curing conditions, the polyether amine and epoxy compound (and optional nylon) polymerize together.

The moisture-sensitive film thus obtained typically has a thickness of up to about 5 μm, especially about 1 to 3.5 μm. This range of thickness ensures sufficient moisture permeation.

As long as the moisture sensor of the invention has the moisture-sensitive film between a pair of electrodes, no particular limit is imposed on its construction. FIG. 1 illustrates one exemplary construction of the moisture sensor.

Referring to FIG. 1, the moisture sensor generally designated at 1 includes an insulating substrate 2 and a pair of comb-shaped electrodes 4 thereon. The pair of comb-shaped electrodes 4 are arranged on the substrate 2 so that they interdigitate with each other via a gap 5 of a predetermined distance. A moisture-sensitive film 3 is formed on the insulating substrate 2 and comb-shaped electrodes 4. A terminal 6 is connected to one end of each electrode 4. A resist film 9 may be provided as shown in the figure.

With the illustrated construction, a voltage is applied to the electrodes. Since the moisture-sensitive film changes its resistance in proportion to a humidity, the humidity is detected from a change of output voltage.

In the illustrated construction, the insulating substrate 2 is made of any desired electrically insulating material which firmly joins with the moisture-sensitive film 3, for example, glass, plastics, ceramics and insulating layer-coated metal.

The electrodes 4 are made of any commonly used material. For example, they are formed by screen printing a low resistance paste containing Au, RuO$_2$ or carbon particles (e.g., carbon black or graphite) and optionally glass frit, followed by high temperature sintering. The electrode terminals 6 are made of Ag—Pd alloy, for example, by printing a paste thereof in a conventional manner and baking at high temperature. The resist film 9 is formed of glass, for example, while its gage and shape are not critical.

The moisture sensor of the invention is not limited to the illustrated one and various structures are employable.

The gap between the pair of electrodes is typically about 0.1 to 1.0 mm.

EXAMPLE

Examples of the invention are given below by way of illustration and not by way of limitation.

The trade names have the following meaning. Jeffamine D400: polyoxypropylene diamine having a number average molecular weight of 400, an amine equivalent of 4.4 meq/g, and a viscosity of 29 centipoise at 20° C., by Texaco Chemical Jeffamine D2000: polyoxypropylene diamine having a number average molecular weight of 2,000, an amine equivalent of 1.0 meq/g, and a viscosity of 342 centipoise at 20° C., by Texaco Chemical Jeffamine D230: polyoxypropylene diamine having a number average molecular weight of 230, an amine equivalent of 8.45 meq/g, and a viscosity of 14 centipoise at 20° C., by Texaco Chemical Jeffamine T403: polyoxypropylene triamine having a number average molecular weight of 440, an amine equivalent of 6.4 meq/g, and a viscosity of 95 centipoise at 20° C., by Texaco Chemical Jeffamine ED600: polyoxyethylene propylene diamine having a number average molecular weight of 600, an EO/PO ratio of 3.4, an amine equivalent of 3.19 meq/g, and a viscosity of 75 centipoise at 20° C., by Texaco Chemical Jeffamine EDR148: polyoxyethylene diamine having a number average molecular weight of 148, an amine equivalent of 13.5 meq/g, by Texaco Chemical Denacol EX-614B: sorbitol polyglycidyl ether having an epoxy equivalent of 180 WPE, a water dissolution of 90%, a viscosity of 4,000 centipoise at 25° C., and a specific gravity of 1.26 at 25° C., by Nagase Chemical K.K.

Denacol EX-411: pentaerythritol polyglycidyl ether having an epoxy equivalent of 231 WPE, a water dissolution of 27%, a viscosity of 760 centipoise at 25° C., and a specific gravity of 1.24 at 25° C., by Nagase Chemical K.K.

KF393: amino-modified silicone oil having a molecular weight of 700 to 1000, by Shin-Etsu Chemical K.K.

PEBAX 4011: polyether ester amide having a specific gravity of 1.14 and a water absorption of 4.5% at 20° C. and RH 65%, by Atochem P-70: water-soluble nylon having a relative viscosity of 2.83 and a water solubility of more than 100 parts by weight per 100 parts by weight of water, by Toray K.K.

A-90: water-soluble nylon having a relative viscosity of 2.71 and a water solubility of more than 100 parts by weight per 100 parts by weight of water, by Toray K.K. Toka Black #4500F: carbon black by Tokai Carbon K.K.

Example 1

To 3 g of ethyl cellosolve were added 0.342 g of polyoxypropylene diamine Jeffamine D400, 0.228 g of polyoxypropylene diamine Jeffamine D2000, and 0.36 g of carbon black Toka Black #4500F. Using a planetary mixer KK-100 (by Kurabo K.K.), the mixture was dispersed for 9 minutes. To the dispersion was added 1.087 g of sorbitol polyglycidyl ether Denacol EX-614B. One minute of dispersion yielded a paste.

Onto an alumina substrate having a pair of comb-shaped electrodes of ruthenium oxide, the paste was applied by screen printing. The coating was then cured at 150° C. for one hour to form a moisture-sensitive film, obtaining a moisture sensor as shown in FIG. 1. The moisture-sensitive film had a dry thickness of 3 μm.

Example 2

To 3 g of ethyl cellosolve were added 0.342 g of polyoxypropylene diamine Jeffamine D400, 0.228 g of polyoxypropylene diamine Jeffamine D2000, 0.36 g of carbon black Toka Black #4500F, and 0.2 g of amino-modified silicone oil KF393. Using a planetary mixer KK-100 (by Kurabo K.K.), the mixture was dispersed for 9 minutes. To the dispersion was added 1.087 g of sorbitol polyglycidyl ether Denacol EX-614B. One minute of dispersion yielded a paste.

Onto an alumina substrate having a pair of comb-shaped electrodes of ruthenium oxide, the paste was applied by screen printing. The coating was then cured at 150° C. for one hour to form a moisture-sensitive film, obtaining a moisture sensor. The moisture-sensitive film had a dry thickness of 3 μm.

Example 3

A moisture sensor was fabricated as in Example 2 except that 0.623 g of polyoxypropylene diamine Jeffamine D400 and 1.377 g of sorbitol polyglycidyl ether Denacol EX-614B were used.

Example 4

A moisture sensor was fabricated as in Example 2 except that 0.423 g of polyoxypropylene diamine Jeffamine D230 and 1.576 g of sorbitol polyglycidyl ether Denacol EX-614B were used.

Example 5

A moisture sensor was fabricated as in Example 2 except that 0.532 g of polyoxypropylene triamine Jeffamine T403 and 1.468 g of sorbitol polyglycidyl ether Denacol EX-614B were used.

Example 6

A moisture sensor was fabricated as in Example 2 except that 0.832 g of polyoxyethylene propylene diamine Jeffamine ED600 and 1.168 g of sorbitol polyglycidyl ether Denacol EX-614B were used.

Comparative Example 1

A paste for moisture-sensitive film was prepared by dissolving 1 g of an alcohol-soluble copolymerized nylon CM4000 (by Toray K.K.) in 10 g of propylene glycol, adding 0.2 g of carbon black Toka Black #4500F, and dispersing the components in a planetary mixer KK-100 (by Kurabo K.K.).

Onto an alumina substrate having a pair of comb-shaped electrodes of ruthenium oxide, the paste was applied by screen printing. The coating was then cured at 150° C. for one hour to form a moisture-sensitive film, obtaining a moisture sensor. The moisture-sensitive film had a dry thickness of 3 μm.

Comparative Example 2

A paste for moisture-sensitive film was prepared by dissolving 1 g of an alcohol-soluble copolymerized nylon CM4000 (by Toray K.K.) in 10 g of propylene glycol, adding 0.3 g of carbon black Toka Black #4500F, and dispersing the components in a planetary mixer KK-100 (by Kurabo K.K.).

Onto an alumina substrate having a pair of comb-shaped electrodes of ruthenium oxide, the paste was applied by screen printing. The coating was then cured at 150° C. for one hour to form a moisture-sensitive film, obtaining a moisture sensor. The moisture-sensitive film had a dry thickness of 3 μm.

Figure 2:
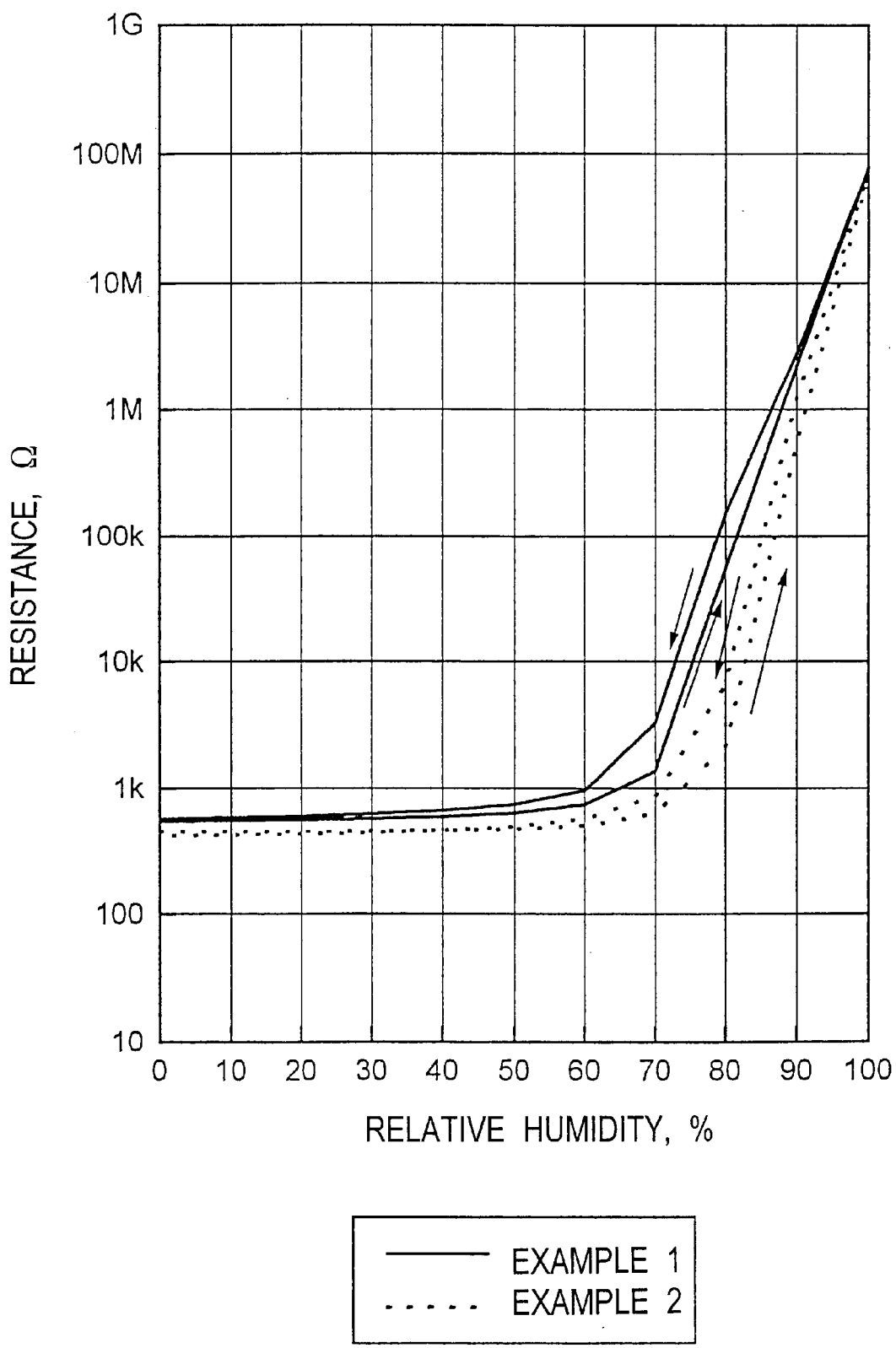
FIG. 2 is a graph showing the humidity-resistance response of moisture sensors of Examples 1 and 2.
Figure 3:
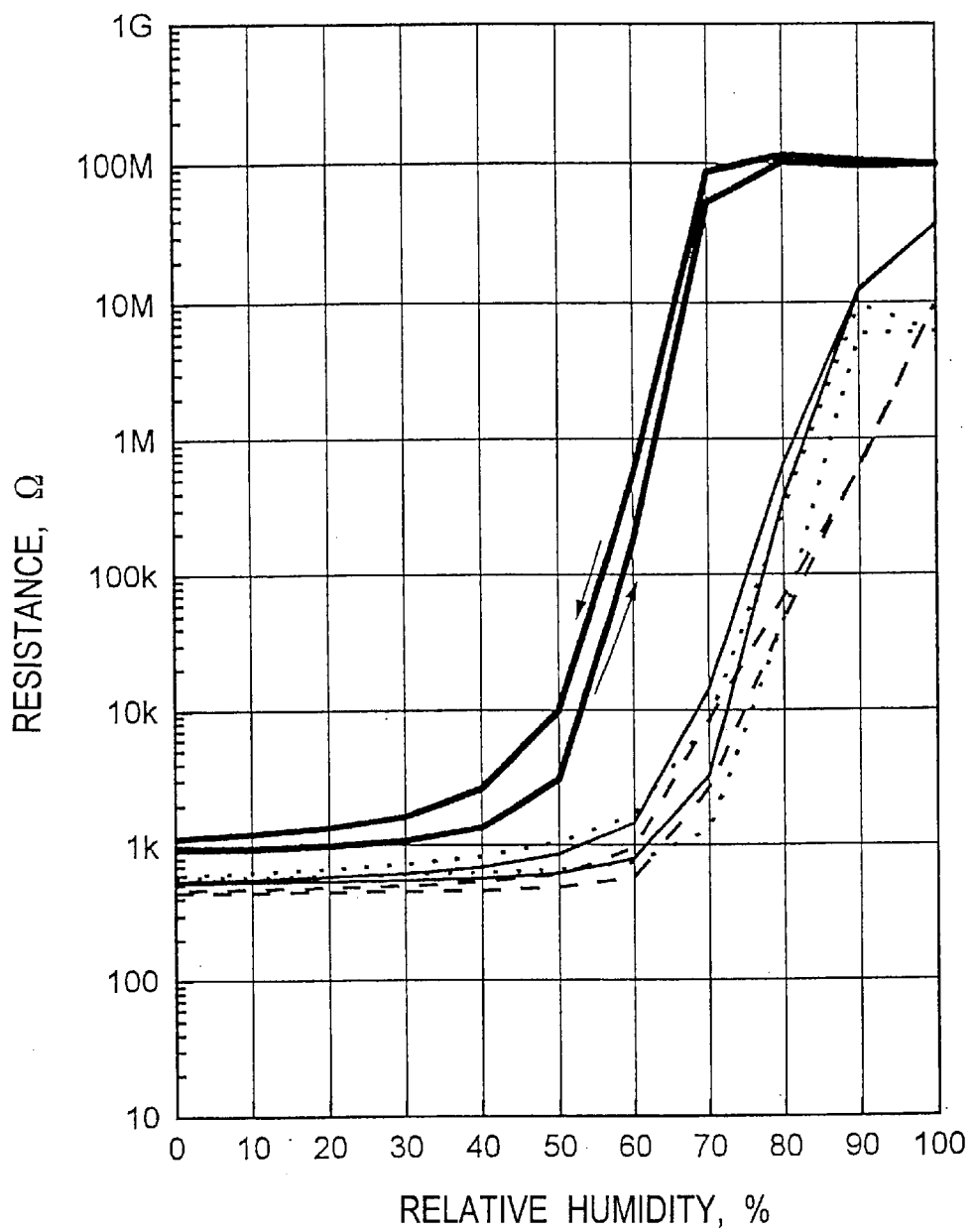
FIG. 3 is a graph showing the humidity-resistance response of moisture sensors of Examples 3 to 6.
Figure 4:
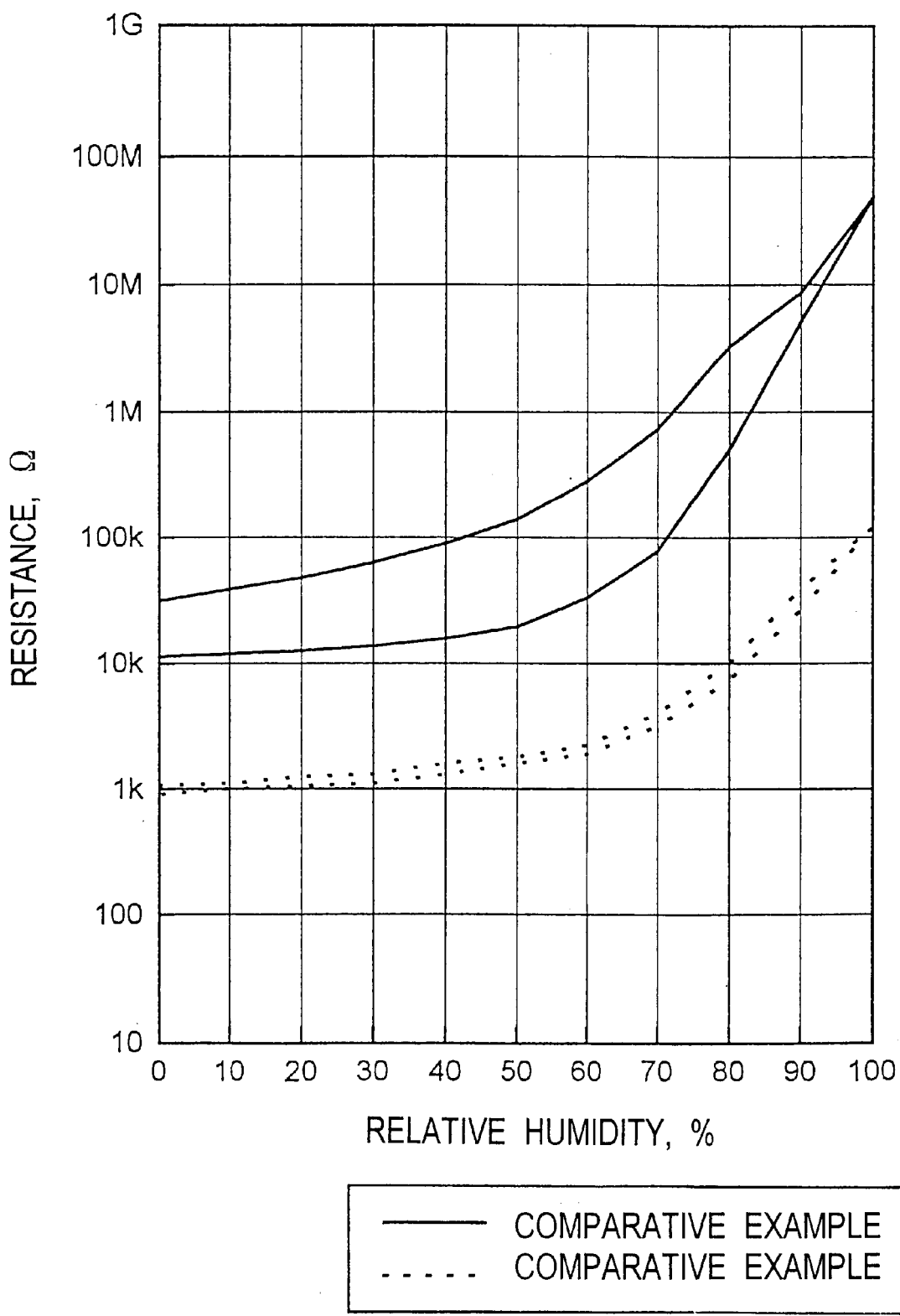
FIG. 4 is a graph showing the humidity-resistance response of moisture sensors of Comparative Examples 1 and 2.

The humidity-resistance response of the sensors thus obtained was examined by operating them in a humid atmosphere while the humidity of the atmosphere was changed between 0% and 100%. FIGS. 2 and 3 show the humidity-resistance response of the moisture sensors of Examples 1 to 6. FIG. 4 shows the humidity-resistance response of the moisture sensors of Comparative Examples 1 and 2. Once the sensor of Comparative Example 1 was exposed to a humidity of RH 100%, it could not resume the original resistance value in a lower humidity atmosphere. The sensor of Comparative Example 2 having a larger loading of carbon black showed less increments of resistance. In contrast, the sensors of Examples 1 to 6 show satisfactory increments of resistance and even after exposed to a humidity of RH 100%, could resume the original resistance value in a lower humidity atmosphere.

Figure 5:
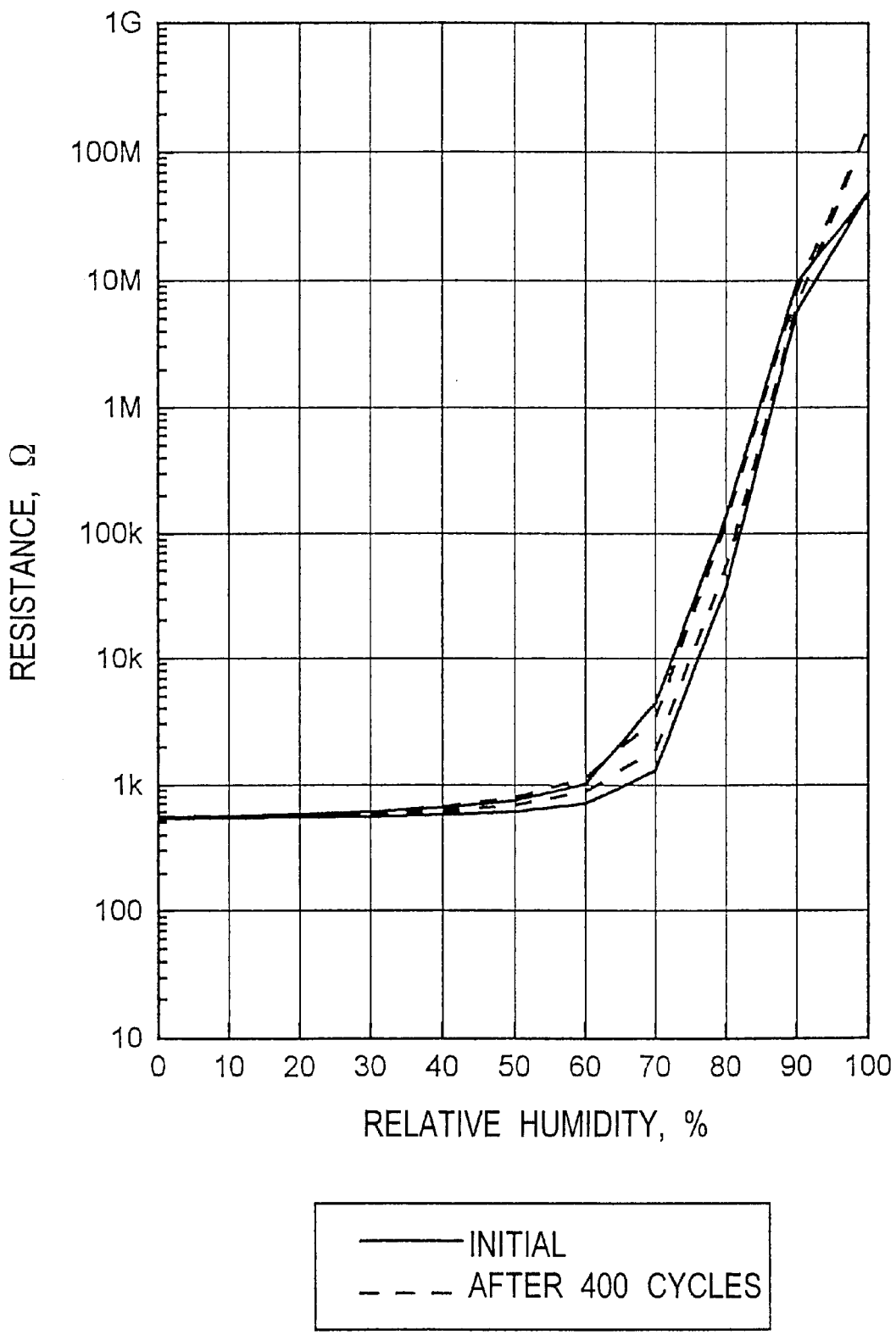
FIG. 5 is a graph showing the humidity-resistance response of the moisture sensor of Example 2 at the initial and after 400 cycles.

FIG. 5 shows the humidity-resistance response of the moisture sensor of Example 2 at the initial and after 400 cycles between an RH 0% atmosphere and an RH 100% atmosphere. The humidity-resistance response remained substantially unchanged even after 400 cycles. Similar results were obtained with the sensors of the remaining Examples 1 and 3 to 6.

Additionally, a moisture sensor was fabricated as in Example 2, but using 0.34 g of polyoxyethylene diamine Jeffamine EDR148 and 1.66 g of sorbitol polyglycidyl ether Denacol EX-614B. The measurement results were similar to those of Example 2.

A further moisture sensor was fabricated as in Example 2, but using 0.351 g of polyoxypropylene diamine Jeffamine D400, 0.234 g of polyoxypropylene diamine Jeffamine D2000, and 1.025 g of polyglycerol polyglycidyl ether Denacol EX-512. The measurement results were similar to those of Example 2.

A still further moisture sensor was fabricated as in Example 2, but using 0.299 g of polyoxypropylene diamine Jeffamine D400, 0.199 g of polyoxypropylene diamine Jeffamine D2000, and 1.168 g of pentaerythritol polyglycidyl ether Denacol EX-411. The measurement results were similar to those of Example 2.

Example 7

To 5 g of ethyl cellosolve were added 2 g of polyether ester amide PEBAX 4011 and 0.32 g of carbon black Toka Black #4500F. The components were dispersed for 10 minutes in a planetary mixer KK-100 (by Kurabo K.K.), yielding a paste.

Onto an alumina substrate having a pair of comb-shaped electrodes of ruthenium oxide, the paste was applied by screen printing. The coating was then cured at 150° C. for one hour to form a moisture-sensitive film, obtaining a moisture sensor as shown in FIG. 1. The moisture-sensitive film had a dry thickness of 3 µm.

This sensor also gave similar measurement results to Example 2.

Example 8

In 3 g of ethyl cellosolve was dissolved 0.05 g of water-soluble nylon P-70. Further added thereto were 0.342 g of polyoxypropylene diamine Jeffamine D400, 0.228 g of polyoxypropylene diamine Jeffamine D2000, and 0.36 g of carbon black Toka Black #4500F. Using a planetary mixer KK-100 (by Kurabo K.K.), the mixture was dispersed for 9 minutes. To the dispersion was added 1.087 g of sorbitol polyglycidyl ether Denacol EX-614B. One minute of dispersion yielded a paste.

Onto an alumina substrate having a pair of comb-shaped electrodes of ruthenium oxide, the paste was applied by screen printing. The coating was then cured at 150° C. for one hour to form a moisture-sensitive film, obtaining a moisture sensor as shown in FIG. 1. The moisture-sensitive film had a dry thickness of 3 µm.

Example 9

In 3 g of ethyl cellosolve was dissolved 0.05 g of water-soluble nylon P-70. Further added thereto were 0.342 g of polyoxypropylene diamine Jeffamine D400, 0.228 g of polyoxypropylene diamine Jeffamine D2000, 0.36 g of carbon black Toka Black #4500F, and 0.2 g of amino-modified silicone oil KF393. Using a planetary mixer KK-100 (by Kurabo K.K.), the mixture was dispersed for 9 minutes. To the dispersion was added 1.087 g of sorbitol polyglycidyl ether Denacol EX-614B. One minute of dispersion yielded a paste.

Onto an alumina substrate having a pair of comb-shaped electrodes of ruthenium oxide, the paste was applied by screen printing. The coating was then cured at 150° C. for one hour to form a moisture-sensitive film, obtaining a moisture sensor. The moisture-sensitive film had a dry thickness of 3 µm.

Example 10

A moisture sensor was fabricated as in Example 9 except that 0.05 g of water-soluble nylon P-70, 0.770 g of polyoxypropylene diamine Jeffamine D400 and 1.230 g of sorbitol polyglycidyl ether Denacol EX-614B were used.

Example 11

A moisture sensor was fabricated as in Example 9 except that 0.05 g of water-soluble nylon P-70, 0.501 g of polyoxypropylene diamine Jeffamine D230 and 1.499 g of sorbitol polyglycidyl ether Denacol EX-614B were used.

Example 12

A moisture sensor was fabricated as in Example 9 except that 0.05 g of water-soluble nylon P-70, 0.612 g of polyoxypropylene triamine Jeffamine T403 and 1.388 g of sorbitol polyglycidyl ether Denacol EX-614B were used.

Example 13

A moisture sensor was fabricated as in Example 9 except that 0.05 g of water-soluble nylon P-70, 0.931 g of polyoxyethylene propylene diamine Jeffamine ED600 and 1.069 g of sorbitol polyglycidyl ether Denacol EX-614B were used.

Figure 6:
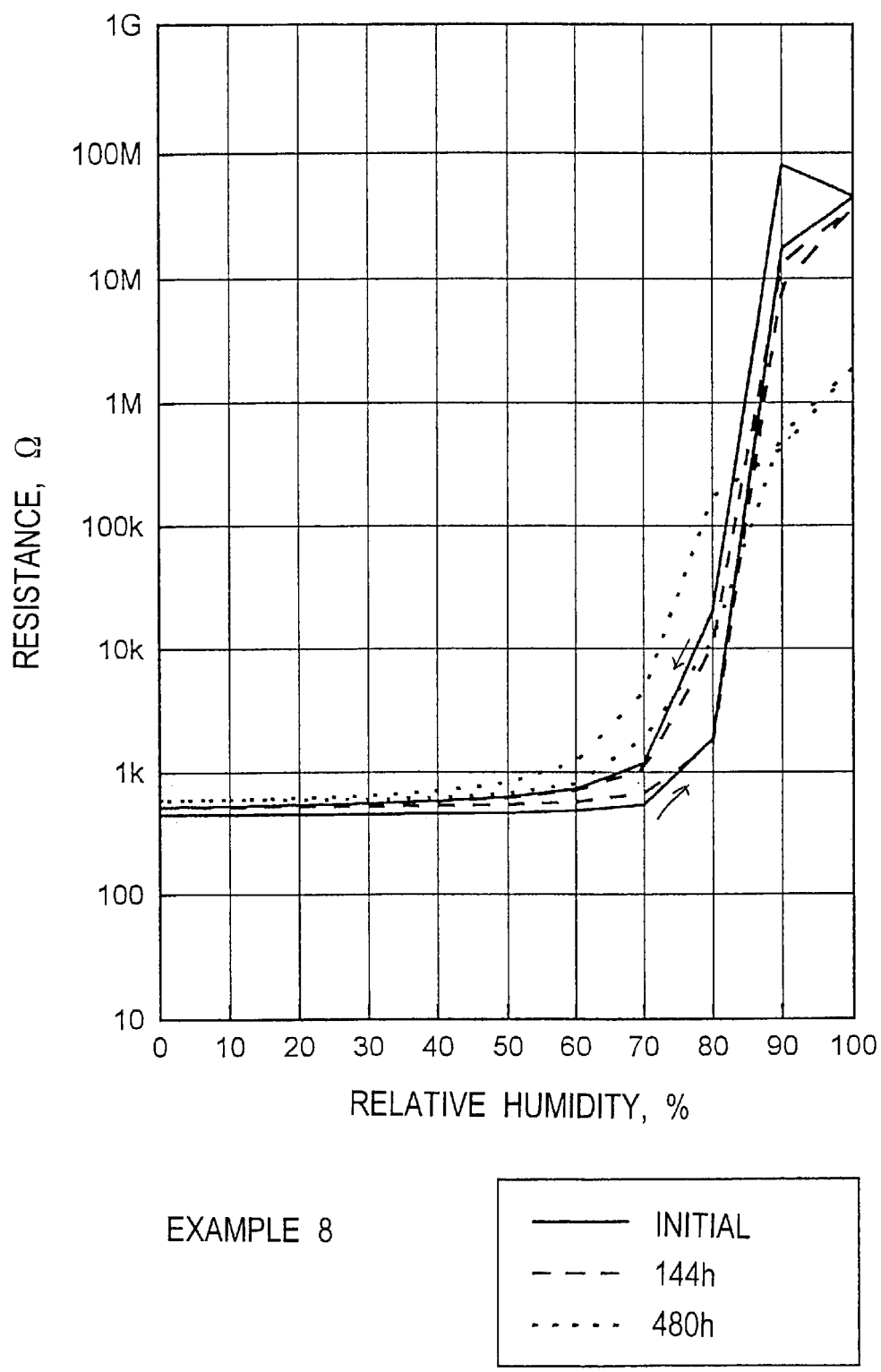
Figure 8:
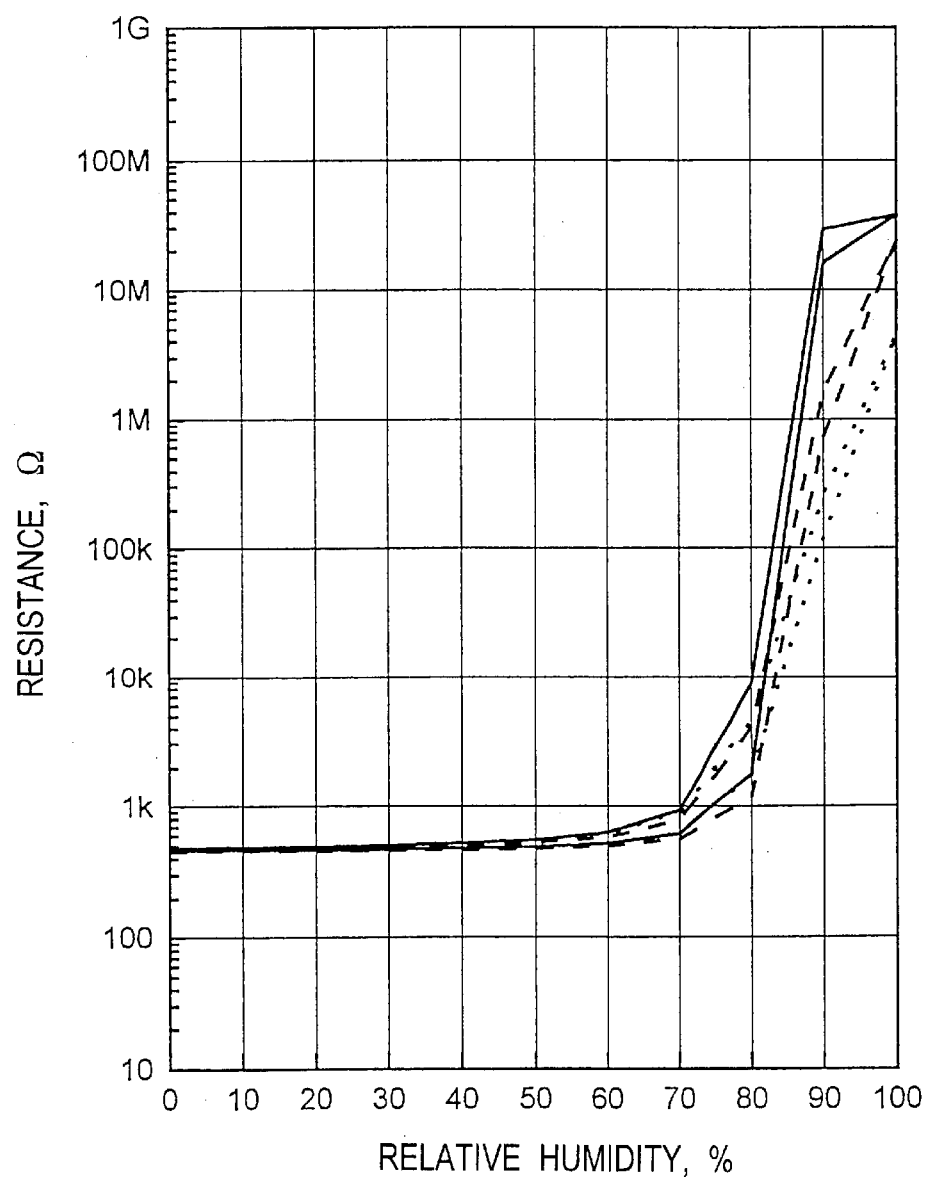

The humidity-resistance response of the sensors thus obtained was examined by operating them in a humid atmosphere while the humidity of the atmosphere was changed between 0% and 100%. This cycling test was performed at the initial and after allowing the sensors to stand for 144 hours and 480 hours in an atmosphere of 60° C. and RH 95%. FIGS. 6 and 11 show the humidity-resistance response of the moisture sensors of Examples 8 to 13 at the initial and after 144 and 480 hours of aging. FIG. 4 shows the humidity-resistance response of the moisture sensors of Comparative Example 1 at the initial. FIG. 12 shows the humidity-resistance response of the moisture sensor of Example 2 at the initial and after 100 hours of aging in an atmosphere of 60° C. and RH 95%. Once the sensor of Comparative Example 1 was exposed to a humidity of RH 100%, it could not resume the original resistance value thereafter. The sensor of Example 2 showed initial characteristics with minimized hysteresis, but experienced a substantial rise of resistance after 100 hours of aging in an atmosphere of 60° C. and RH 95%. In contrast, the sensors of Examples 8 to 13 show showed initial characteristics with minimized hysteresis, and the change of their humidity-resistance response was suppressed to a practically acceptable level even after 488 hours of aging in an atmosphere of 60° C. and RH 95%

Additionally, a moisture sensor was fabricated as in Example 9, but using 0.05 g of water-soluble nylon P-70, 0.34 g of polyoxyethylene diamine Jeffamine EDR148 and 1.66 g of sorbitol polyglycidyl ether Denacol EX-614B. The measurement results were similar to those of Example 9.

A further moisture sensor was fabricated as in Example 9, but using 0.05 g of water-soluble nylon P-70, 0.351 g of polyoxypropylene diamine Jeffamine D400, 0.234 g of polyoxypropylene diamine Jeffamine D2000, and 1.025 g of polyglycerol polyglycidyl ether Denacol EX-512. The measurement results were similar to those of Example 9.

A still further moisture sensor was fabricated as in Example 9, but using 0.05 g of water-soluble nylon P-70, 0.299 g of polyoxypropylene diamine Jeffamine D400, 0.199 g of polyoxypropylene diamine Jeffamine D2000, and 1.168 g of pentaerythritol polyglycidyl ether Denacol EX-411. The measurement results were similar to those of Example 9.

Still further moisture sensors were fabricated as in Example 9, but using 0.05 g of water-soluble nylon A-90. The measurement results were similar to those of Example 9.

Example 14

In 5 g of ethyl cellosolve was dissolved 0.05 g of water-soluble nylon P-70. Further added thereto were 2 g of polyether ester amide PEBAX 4011 and 0.32 g of carbon black Toka Black #4500F. The components were dispersed for 10 minutes in a planetary mixer KK-100 (by Kurabo K.K.), yielding a paste.

Onto an alumina substrate having a pair of comb-shaped electrodes of ruthenium oxide, the paste was applied by screen printing. The coating was then cured at 150° C. for one hour to form a moisture-sensitive film, obtaining a moisture sensor as shown in FIG. 1. The moisture-sensitive film had a dry thickness of 3 μm.

This sensor also gave similar measurement results to Example 9.

The moisture sensors of the first and second embodiments allow for DC measurement, can detect a humidity in a region below RH 90%, especially in the humidity region of RH 60% to 100%, and ensure high performance stability against repetitive operations. The sensors of the preferred embodiments experience little deterioration of performance even in a high temperature, high humidity atmosphere.

Japanese Patent Application Nos. 10-377081 and 10-377082 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A moisture sensor comprising a pair of electrodes and a moisture-sensitive film disposed therebetween having conductive particles dispersed in a hygroscopic polymer composition comprising a polyether amine having at least two amino groups, and an epoxy compound having at least two epoxy groups and an ether bond.

2. The moisture sensor of claim 1 wherein said polyether amine has a polyether skeleton consisting of propylene oxide, ethylene oxide or a mixture thereof.

3. The moisture sensor of claim 1 wherein said polyether amine is terminated with two or three primary amino groups.

4. The moisture sensor of claim 1 wherein said polyether amine has a molecular weight of 100 to 5,000.

5. The moisture sensor of claim 1 wherein said epoxy compound is of the following formula (1):

$$A \!-\!\!\left(\! O\!-\!CH_2\!-\!\underset{O}{CH\!-\!CH_2} \!\right)_{\!k} \quad (1)$$

wherein A is a di- to tetra-valent aliphatic saturated hydrocarbon group, aliphatic ether group or heterocyclic group, and k is an integer of 2 to 4.

6. The moisture sensor of claim 1 wherein said hygroscopic polymer has an amine equivalent and an epoxy equivalent which are in a ratio of from 1:1 to 1:4.

7. The moisture sensor of claim 1 wherein said hygroscopic polymer composition additionally comprises a water-soluble nylon.

8. The moisture sensor of claim 7 wherein said water-soluble nylon has an ether structure.

9. The moisture sensor of claim 7 wherein said water-soluble nylon comprises units of the following formula (7) or units of the following formula (8) or both:

$$-\!\!\left[\!NH(CH_2)_3OR_1O(CH_2)_3NHOC(CH_2)_4CO\!\right]\!\!- \quad (7)$$

$$-\!\!\left[\!NH(CH_2)_5CO\!\right]\!\!- \quad (8)$$

wherein $R_1$ is an alkyl group of 2 to 4 carbon atoms.

10. The moisture sensor of claim 7 wherein the content of the water-soluble nylon is 0.1 to 50% by weight based on the weight of said polyether amine and said epoxy compound combined.

11. The moisture sensor of claim 1 wherein said conductive particles comprise carbon black having a specific surface area of 30 to 300 $m^2/g$.

12. The moisture sensor of claim 1 which can detect a humidity in the range of RH 60% to RH 100%.

13. A moisture sensor comprising a pair of electrodes and a moisture-sensitive film disposed therebetween having conductive particles dispersed in a hygroscopic polymer composition comprising a polyether ester amide.

14. The moisture sensor of claim 13 wherein said polyether ester amide is of the following formula (2):

$$HO\!-\!\!\left[\!\left[\!CO(CH_2)_mNH\!\right]_p\!-\!CO\!-\!R\!-\!COO\!-\!\left[(CH_2)_nO\!\right]_q\!\right]_r\!-\!H \quad (2)$$

wherein R is an alkyl group of 2 to 12 carbon atoms, m is an integer of 6 to 12, n is an integer of 1 to 4, p is an integer of 1 to 70, q is an integer of 5 to 200, and r is an integer of at least 3.

15. The moisture sensor of claim 14 wherein in formula (2), m is equal to 11 and n is equal to 2.

16. The moisture sensor of claim 13 wherein said hygroscopic polymer composition additionally comprises a water-soluble nylon, and an epoxy compound having at least two epoxy groups.

17. The moisture sensor of claim 13 wherein said hygroscopic polymer composition is a mixture of the polyether ester amide and a water-soluble nylon.

18. The moisture sensor of claim 16 or 17 wherein said water-soluble nylon has an ether structure.

19. The moisture sensor of claim 16 or 17 wherein said water-soluble nylon comprises units of the following formula (7) or units of the following formula (8) or both:
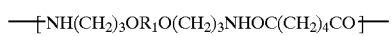 (7)
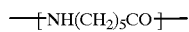 (8)
wherein $R_1$ is an alkyl group of 2 to 4 carbon atoms.
20. The moisture sensor of claim 16 or 17 wherein the content of the water-soluble nylon is 0.1 to 50% by weight based on the weight of said polyether ester amide.
* * * * *